United States Patent [19]

Higuchi

[11] 4,210,139
[45] Jul. 1, 1980

[54] OSMOTIC DEVICE WITH COMPARTMENT FOR GOVERNING CONCENTRATION OF AGENT DISPENSED FROM DEVICE

[75] Inventor: Takeru Higuchi, Lawrence, Kans.
[73] Assignee: Alza Corporation, Palo Alto, Calif.
[21] Appl. No.: 4,180
[22] Filed: Jan. 17, 1979
[51] Int. Cl.² .............................................. A61M 7/00
[52] U.S. Cl. .................................................... 128/260
[58] Field of Search .................. 128/222, 213 R, 260, 128/261, 268; 424/19

[56] References Cited
U.S. PATENT DOCUMENTS

| | | | |
|---|---|---|---|
| 3,732,865 | 5/1973 | Higuchi et al. | 128/260 |
| 4,111,202 | 9/1978 | Theeuwes | 128/260 |

Primary Examiner—Robert W. Michell
Assistant Examiner—C. F. Rosenbaum
Attorney, Agent, or Firm—Paul L. Sabatine; Thomas E. Ciotti; Edward L. Mandell

[57] ABSTRACT

An osmotic device is disclosed for dispensing a drug. The device comprises an exterior wall surrounding a first and second compartment. The first compartment is in contact with the exterior wall and the second compartment is surrounded by an interior wall that is in contact with the exterior wall. A passageway exists through the exterior wall connecting the first compartment with the exterior of the device, and a passageway exists through the interior wall connecting the second with the first compartment. The first compartment contains an osmotic solute that exhibits an osmotic pressure gradient across the wall against an external fluid, and the second compartment contains a drug that exhibits an osmotic pressure gradient across the wall against the fluid. The exterior and the interior walls are permeable to the passage of the fluid, and they are impermeable to the passage of solute and drug, but the rate of fluid, permeability is greater through the exterior than through the interior wall. In operation, fluid in imbibed through the walls into the compartments and at a greater rate into the first compartment forming a more dilute solution therein than the drug solution formed in the second compartment, said drug solution passing from the second compartment through the passageway into the compartment and being diluted in the first compartment, with the diluted drug solution passing from the first compartment through the passageway to the exterior of the device.

6 Claims, 4 Drawing Figures

OSMOTIC DEVICE WITH COMPARTMENT FOR GOVERNING CONCENTRATION OF AGENT DISPENSED FROM DEVICE

FIELD OF THE INVENTION

This invention pertains to an osmotic device. More particularly, the invention relates to an osmotic device for dispensing drugs that are irritants to mucosal tissue and the tissue of gastrointestinal tract. Specifically, the device comprises a first and second compartment that act together for dispensing a diluted drug solution, thereby lessening the incidence of irritation to the tissues.

BACKGROUND OF THE INVENTION

There are many drugs known to pharmaceutical science that are used for producing a beneficial effect and have serious shortcomings associated with their use. For example, the electrolyte potassium chloride is the salt most frequently used when the action of the potassium cation is desired for an indicated therapeutic effect. Potassium chloride is used when hypokalemia exists, as a treatment with certain diuretics, in steroid therapy and for relieving the symptoms of Meniers's disease. However, serious shortcomings are associated with its use, mainly concentrated preparations of potassium chloride are an irritant to the gastrointestinal tract and its use often leads to bowel lesions. Another important drug that possesses similar shortcomings is aspirin. Aspirin, or acetalsalicylic acid, is widely used as an antipyretic and analgetic in a variety of medical conditions. Aspirin is a very potent drug; however, occult gastrointestinal bleeding often follows use of conventional, concentrated dosage forms of the drug. One additional example of a useful drug whose usefulness often is comprised by unwanted effects is indomethacin. Indomethacin is a nonsteroid indole that exhibits both analgesic and anti-inflammatory properties, and it is used for the treatment of rheumatoid arthritis. The most frequent untoward actions associated with concentrated dosage forms containing this drug are gastrointestinal disturbances similar to those mentioned above. In the light of this presentation, it will be appreciated by those versed in the dispensing art that if a device were made available for dispensing drugs in less than concentrated amounts, such a device would have a definite use and represent a valuable contribution to the art.

OBJECTS OF THE INVENTION

Accordingly, it is an immediate object of this invention to provide an osmotic device that overcomes the problems associated with the prior art and which device can be used for dispensing a drug to a biological environment of use.

Another object of the present invention is to provide an improvement in drug delivery by making available an osmotic device for the controlled and continous delivery of a beneficial drug in a diluted amount over a prolonged period of time.

Yet another object of this invention is to provide an osmotic device consisting of a first compartment that is a means for diluting the concentration of a drug solution that enters the first compartment from a second compartment, which diluted drug solution is then dispensed form the device.

Still another object of the invention is to provide an osmotic device that in operation in situ can significantly reduce the high concentration of a drug solution to a more dilute drug solution which diluted solution has a correspondingly decreased ability to produce injury to the tissues of the gastrointestinal tract.

Other objects, features, aspects and advantages of the invention will be more apparent to those versed in the art from the following detailed specification, taken in conjunction with the figures and the accompanying claims.

SUMMARY OF THE INVENTION

This invention concerns an osmotic device for dispensing a drug to an environment of use. The system comprises an outer semipermeable wall surrounding two adjoining compartments, forming one single-walled compartment and the other compartment surrounded by an additional inner semi-permeable wall forming a two-walled compartment. The outer wall possesses a greater permeability to the passage of fluid than the inner wall. A passageway in the outer wall connects the exterior of the device with the single-walled compartment, and a passageway in the inner wall connects the two compartments. A drug present in the two-walled compartment is released by the combined action of fluid being imbibed through the walls into each compartment, and at a greater rate into the single-walled compartment that into the two-walled compartment, thereby producing a solution in each compartment. The drug solution in the two-walled compartment passes through the passageway into the single-walled compartment and is diluted therein, with the diluted drug solution passing through the passageway form the single-walled compartment to the exterior of the device.

BRIEF DESCRIPTION OF THE DRAWINGS

In the drawings, which are not drawn to scale, but are set forth to illustrate various embodiments of the invention, the figures are as follows.

In the drawings and specification, like parts in related figures are identified by like parts. The terms appearing earlier in the specification and in the description of the drawings, as well as embodiments thereof, are further detailed elsewhere in the disclosure.

DETAILED DESCRIPTION OF THE DRAWINGS

Figure 1:
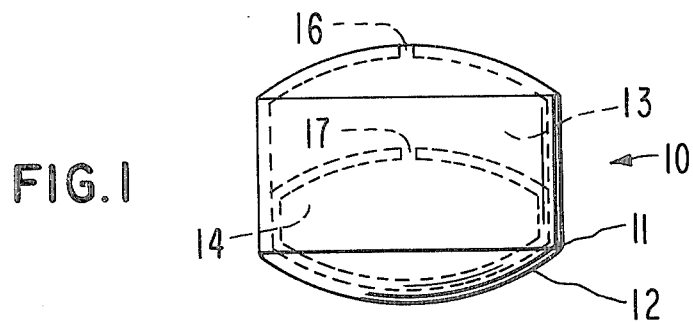
FIG. 1 is a view of an osmotic device designed for orally administering a beneficial drug to a warm-blooded animal.

Turning now to the drawings in detail, which are examples of various osmotic delivery devices of the invention, and which examples are not to be considered as limiting, one example of an osmotic device is indicated in FIG. 1 by the numeral 10. In FIG. 1, device 10 comprises a body 11 that can be shaped, sized, adapted and structured for placement and prolonged retention in a biological environment of use for the controlled delivery of drug thereto. The dashed lines seen in FIG.

1 indicate the structure of device 10 as discussed below in FIGS. 2a and 2b.

Figure 2A:
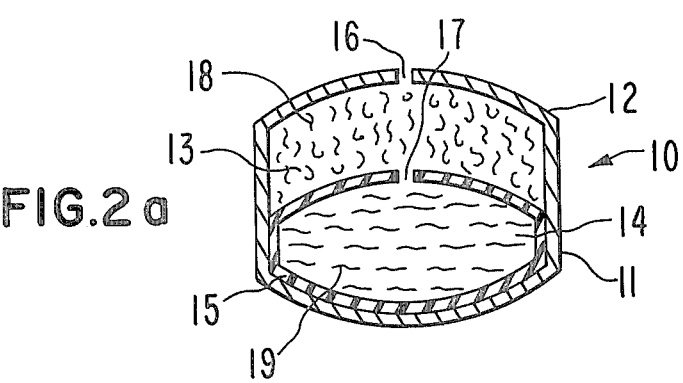
FIG. 2a and FIG. 2b are opened views of FIG. 1, which Figures illustrate the compartments and structure of the device manufactured as an integrally formed device.
Figure 2B:
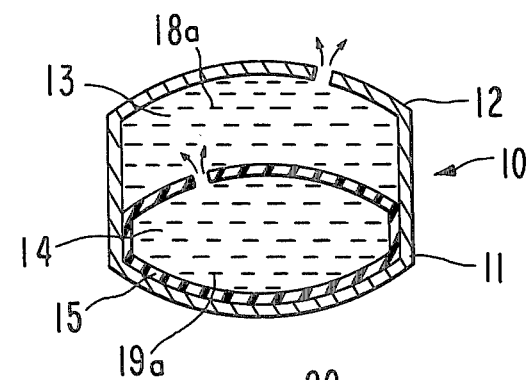

In FIGS. 2a and 2b, device 10 is seen in full opened-section. In these Figures, device 10 comprises a body 11 having an exterior wall 12 that surrounds and forms a first compartment 13 and a second compartment 14. The second compartment 14 additionally is surrounded by an interior wall 15 that further defines and forms compartment 14. Both exterior wall 12 and interior wall 15 are formed of a semipermeable polymer that is permeable to the passage of an external fluid, and impermeable to the passage of both an osmotically effective solute and drug, but the rate of passage of fluid through exterior wall 12 is greater than the rate of passage through interior wall 15.

Device 10 has a pair of passageways. A passageway 16 in exterior wall 12 connects the first compartment 13 with the exterior of device 10, and a passageway 17 in interior wall 15 connects first compartment 13 with second compartment 14. Compartment 13 contains an osmotic effective agent or solute 18 that exhibits an osmotic pressure gradient across wall 12 against an external fluid and 18 is in direct contact with wall 12. Compartment 14 contains a drug 19 that exhibits an osmotic pressure gradient across wall 12 and wall 15 against an external fluid and 19 is in direct contact with interior wall 15. When, drug 19 exhibits limited solubility or it is substantially insoluble in the external fluid, drug 19 can be mixed with an innocuous osmotically effective solute that exhibits an osmotic pressure gradient across walls 12 and 15.

In operation, compartment 13 and compartment 14 operate together to delivery drug 19 from device 10. That is, external fluid is imbibed into compartment 13 in a tendency towards osmotic equilibrium at a rate controlled by the permeability of wall 12 and the osmotic pressure gradient across wall 12 to dissolve solute 18 and form osmotic solute solution 18a. External fluid is simultaneously imbibed into compartment 14 in a tendency towards osmotic equilibrium at a lesser rate than into compartment 13. The rate into compartment 14 is controlled by the permeabilities of walls 12 and 15 and the osmotic pressure gradient across walls 12 and 15 thereby dissolving drug 19 and forming drug solution 19a. Drug solution 19a is osmotically pumped from compartment 14 through passageway 17 into compartment 13 where it mixes with and is diluted by solution 18a. The diluted drug solution then is osmotically pumped from compartment 13 through passageway 16 to the exterior of device 10.

System 10 of FIG. 1 and FIGS. 2a and 2b can be made into many embodiments, including the presently preferred embodiments for oral use. Device 10 can be used for releasing either a locally or systemically acting therapeutic drug in the gastrointestinal tract over a prolonged period of time. Device 10 can have conventional oral shapes and sizes such as round with a diameter of 3/16 inch to ½ inch, or it can be shaped like a capsule having a range of sizes from triple zero, and from 1 to 8. In these forms, device 10 can be adapted for administering drug to numerous animals, avians, fishes and reptiles. The term animals as used herein includes warm-blooded animals, mammals and humans.

Figure 3:
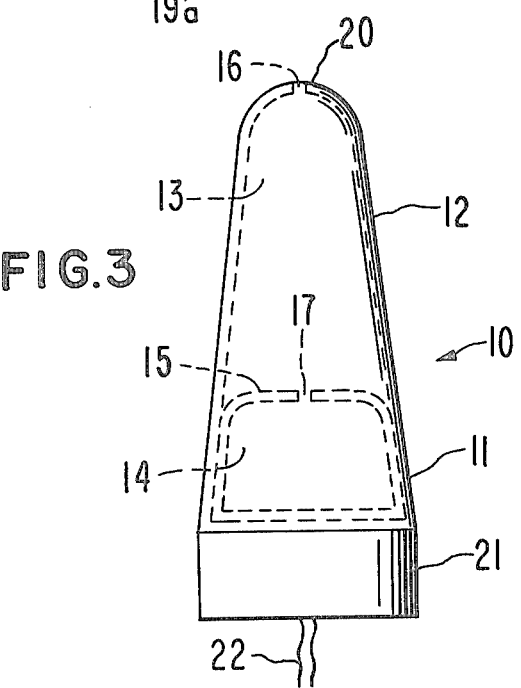
FIG. 3 illustrates an osmotic device provided by the invention designed for dispensing a drug in a body passageway such as the vagina or ano-rectal passageway.

FIG. 3 shows an osmotic device 10 designed for placement in a body passageway, such as the vagina or the ano-rectal passage. Device 10 has an elongated, cylindrical, self-sustaining shape with a rounded lead end 20, a trailing base end 21, and it is equipped with a manually controlled cord 22 for easily removing device 10 from the body passage. Device 10 of FIG. 3 is structurally identical with device 10 of FIGS. 1, 2a and 2b, as described above, and it operates in a like manner. Device 10 of FIG. 3 in one embodiment contains a drug designed for absorption by the vaginal mucosa or the rectal mucosa.

While FIGS. 1 through 3 are illustrative of various devices that can be made according to the invention, it is to be understood those devices are not to be construed as limiting the invention, as the devices can take a wide variety of shapes, sizes and forms for delivering drug- to different biological environments of use. For example, the devices include buccal, implant, eye, artificial gland, cervical, intrauterine, ear, nose, dermal, subcutaneous and blood delivery devices. The devices can be used in hospitals, veterinary clinics, nursing homes, sickrooms, and the like.

DETAILED DESCRIPTION OF THE INVENTION

In accordance with the practive of the invention, it has now been found that osmotic delivery system 10 can be manufactured with a wall 12 formed of a material that does not adversely affect the osmotic solute, drug, animal or other host, and is permeable to an external fluid such as water and biological fluids while remaining impermeable to solutes and drugs. The selectively permeable materials forming exterior semipermeable wall 12 are materials insoluble in body fluids and they are non-erodible, or they can be made to bioerode after a preditermined period with the bioerosion occurring at the end of the drug delivery period. Typical materials for forming wall 12 include semipermeable polymers, also known to the art as osmosis membranes. The semipermeable polymers include cellulose acylate, cellulose diacylate, cellulose triacylate, cellulose ethers and cellulose esters. Typical semipermeable polymers include cellulose acetate, cellulose diacetate, cellulose triacetate, dimethyl cellulose acetate, cellulose acetate ethyl carbamate, and the like. Other semipermeable polymers include polyurethane, and selectively permeable polymers formed by the coprecipitation of a polycation and a polyanion. Generally, semipermeable polymers useful for forming wall 12 will have a fluid permeability of $10^{-5}$ to $10^{-1}$ (cc.mil/cm$^2$·hr·atm) expressed per atmosphere of hydrostatic or osmotic pressure difference across wall 12 at the temperature of use.

Further, in accordance with the practice of the invention, interior semipermeable wall 15 is independently selected from semipermeable homopolymers and semipermeable copolymers that exhibit different operable properties than the polymer forming wall 12. Representative materials suitable for forming wall 15 include polymeric cellulose esters and copolymeric cellulose esters such as mono, di and triacylates, and cellulose ethers. These materials include cellulose actate, cellulose diacetate, cellulose triacetate, cellulose propionate, cellulose acetate propionate, cellulose acetate butyrate, cellulose trivalerate, cellulose dipalmitate, and the like.

Those versed in the art to which this invention pertains can select a semipermeable polymer for forming wall 12 that possesses a different degree of permeability to the passage of fluid that the semipermeable polymer forming wall 15 by using the following criterions. The scientific criterions are: (a) the polymer possesses a high degree of substitution, for example, the polymer has undergone etherification or esterification particularly acylation towards or to completion with the polymer formed demonstrating increased resistance to the passage of fluid; (b) the polymer exhibits a flux decrease with increasing molecular size of the substituting group, such as an ether or ester group; (c) the polymer exhibits a flux decrease proportional to the increase in size of the substituent, for example, the decrease occurs as the number of carbon atoms increase in a hydrocarbon moiety such as as alkyl or alkoxy moiety; (d) the polymer exhibits decreased flux with an increase in the degree of substitution of hydrophobic ether and larger hydrophobic ester groups; and (e) the polymer exhibits a flux decrease as the number of polar, ionic groups bonded to the polymer decreases.

The flux of a fluid, for example, the rate of water vapor transmission through various wall forming polymers also is ascertainable by using the procedure described in *Diffusion in Polymers*, pages 1 to 39, and then expressing the results of as WVTR, or water vapor transmission rate through a film of the polymer in grams/100 in²/24 hr/one mil thick film. Known WVTR values can also be found in *Plastic Film Technology*, by Park, W. W. R, 1969, published by Van Nostrand-Reinhold Inc., and in *Diffusion in Polymers*, by Crank J., and Park G. S., pages 274 to 276, published by Academic Press. Typical values are set forth in Table 1 immediately below wherein the film is the wall forming polymer and WVTR is as defined.

TABLE 1

| Film | WVTR |
|---|---|
| Polyvinyl alcohol | 100 |
| Polyurethane | 30–50 |
| Methylcellulose | 70 |
| Cellulose acetate | 40–75 |
| Ethylcellulose | 75 |
| Cellulose acetate butyrate | 50 |
| Polyvinylchloride, cast | 10–20 |
| Polyvinylchloride, extruded | 6–15 |
| Polycarbonate | 8 |
| Polyvinylfluoride | 3 |
| Ethylene vinyl acetate | 1–3 |
| Polyesters | 2 |
| Cellophane, polyethylene coated | >1.2 |
| Polyvinylidene fluoride | 1.0 |
| Polyethylene | 0.5–1.2 |
| Ethylene propylene copolymer | 0.8 |
| Polypropylene | 0.7 |
| Polyvinyl chloride, rigid | 0.7 |

Another criterion that can be used for measuring the fluid permeability of different polymeric films consists in using a standard osmosis cell. The measurement is carried out by using the osmosis cell and measuring the rate of fluid through a membrane made of wall forming polymer having a known composition and thickness. The flow rate is determined by measuring fluid transport from a first chamber containing a fluid free of agent through a polymer membrane that separates it from a second chamber housing a solution containing a known concentration of a drug or a solute that exhibits an osmotic pressure gradient across the membrane. The flow measurement is preformed by adding to the first chamber the fluid and then adding to the second chamber, equipped with a stirring bar, the same fluid containing drug, and optionally containing an additional osmotic solute. The first chamber is connected through a conduit to a reservoir containing a supply of fluid, and the second chamber is connected to a vertically positioned tube of known diameter and calibrated with indicia that indicate the amount of fluid in the tube. In operation, fluid flows from the first chamber, through the membrane into the second chamber by osmosis causing the solution to rise over time, t, to give a volume displacement $\Delta V$, during a time interval, $\Delta T$. The volume, $\Delta T$. The volume, $\Delta V$, is read on the tube calibrated in cm³, and the time interval, $\Delta T$, is measured with a stopwatch. The value $k_o \pi$ in cm³·mil/cm²·hr for the membrane with permeability, $k_o$, for the drug solution with an osmotic pressure, $\pi$, is calculated from Equation 1, and wherein $A_o$ is the area of the membrane in the diffusion cell, and $h_o$ is the thickness of the membrane.

$$k_o \pi = \Delta V / \Delta t \cdot h_o / A_o \qquad \text{Eq.1}$$

If the measured value, $k_o \pi$, approximates the calculated value, $k\pi$, the membrane can be used for manufacturing the osmotic device. Osmotic flow procedures are described in *J. App. Poly. Sci.*, Vol. 9, pages 1341 to 1362, 1965; and in *Yale J. Biol. Med.*, Vol. 42, pages 139 to 153, 1978.

The osmotically effective solutes, or compounds, that can be used in first compartment 13 for the purpose of the invention include inorganic and organic compounds that exhibit an osmotic pressure gradient across a semipermeable wall against an external fluid. Osmotically effective solutes useful for the present purpose include magnesium sulfate, lactose, mannitol, urea, inositol, carbohydrates such as raffinose, sucrose, glucose, lactose, sorbitol, mixtures thereof, and the like. The osmotic pressure of saturated solutions of various osmotically effective solutes and for mixtures of compounds at 37° C., in water, is listed in Table 2. In the table, the osmotic pressure $\pi$ is in atmospheres, ATM. The osmotic pressure is measured in a commercially available osmometer that measures the vapor pressure difference between pure water and the solution to be analyzed and according to standard thermodynamic principles, the vapor pressure ratio is converted into osmotic pressure difference. In Table 2, osmotic pressures of from 30 ATM to 500 ATM are set forth, of course, the invention includes the use of lower osmotic pressures and higher osmotic pressures than those set forth by way of example in Table 2. Those versed in the art can easily select an osmotic solute, or determine the exhibited osmotic pressure of a drug with an osmometer. The osmometer used for the present measurements is identified as Model 302B, Vapor Pressure Osmometer, manufactured by the Hewlett Packard Co., Avondale, Pa.

TABLE 2

| Compound or Mixture | Osmotic Pressure ATM |
|---|---|
| Lactose-Fructose | 500 |
| Destrose-Fructose | 450 |
| Sucrose-Fructose | 430 |
| Mannitol-Fructose | 415 |
| Sodium Chloride | 356 |
| Fructose | 355 |
| Lactose-Sucrose | 250 |
| Potassium Chloride | 245 |
| Lactose-Dextrose | 225 |
| Mannitol-Dextrose | 225 |
| Dextrose-Sucrose | 190 |
| Mannitol-Sucrose | 170 |
| Sucrose | 150 |
| Mannitol-Lactose | 130 |
| Dextrose | 82 |
| Potassium Sulfate | 39 |
| Mannitol | 38 |

TABLE 2-continued

| Compound or Mixture | Osmotic Pressure ATM |
| --- | --- |
| Sodium Phosphate Tribasic . 12H$_2$O | 36 |

The term drug as used in this specification and the accompanying claims include any physiologically or pharmacologically active substance that produces a localized or systemic effect, or effects in animals, including mammals, humans, primates, farm animals, sport animals and zoo animals. The active drugs that can be delivered include inorganic and organic compounds without limitation, these materials act on the nervous system, they are hypnotics, sedatives, psychic energizers, tranquilizers, anti-convulsants, muscle relaxants, antiparkinson, antipyretics, anti-inflammatory, analgesics, anesthetics, muscle contractants, hormones, steroids, anti-microbials, sympathomimetic, cardiovascular, diuretics, neoplastics, hypoglycemics, amino acids, ophthalmic, vitamins, and the like. The beneficial drugs, and the amount to be delivered are known to the art in *Pharmaceutical Sciences,* by Remington, 14th Ed, 1970, published by Mack Publishing Co., Easton, Pa.; and in *The Pharmacological Basis of Therapeutics,* by Goodman and Gilman, 4th Ed., 1970, published by The MacMillian Company, London.

The expression passageway as used herein comprises means and methods suitable for releasing the drug from the device, and for transporting drug from the second compartment to the first compartment. The expression includes aperture, orifice, bore, or a passageway formed in situ by eroding a water soluble plug, such as a gelatin plug. A detailed description of osmotic passageway, that permits the device to function according to osmotic principles, and the maximum and minimum dimensions for a passageway are disclosed in U.S. Pat. Nos. 3,845,770 and 3,916,899.

The devices of the invention are manufactured by standard techniques. For example, in one embodiment drug housed in the second compartment and a solvent are mixed into a solid, semi-solid or pressed into a shaped form, by conventional methods. The techniques used to make the drug forming compartment include ballmilling, calendering, stirring or rollmilling, and then pressed or tableted into a preselected shape. The wall forming material can be applied by molding, spraying or dipping the pressed shape into the wall forming material. In another embodiment, a wall can be cast, shaped to the desired dimensions that surround compartment 14, the compartment filled with drug, closed and a passageway drilled through the wall. An exterior wall can then be cast, shaped to the desired dimensions to surround and form compartment 13 and 14. Finally, compartment 13 is filled with an osmotic solute, and a passageway drilled through the exterior wall connecting compartment 13 with the exterior of the device.

In a presently preferred embodiment, the device is made by using air suspension techniques. This procedure consists in compressing drug, and then suspending and tumbling the drug in an interior wall forming composition until this wall is applied around the drug. Next, after drying, a passageway is drilled in this wall. Then, an osmotic solute is compressed over the side of the wall having the passageway, and the article returned to the air suspension machine, suspended and tumbled in a current of air until the external wall is formed around the two compartments. After drying, a passageway is drilled in the external wall connecting the solute compartment with the exterior of the device. The air suspension procedure is described in U.S. Pat. No. 2,799,241; in *J. Am. Pharm. Assoc.,* Vol. 48, pages 451 to 459, 1959; and ibid., Vol. 49, pages 82 to 84, 1960. Other wall forming techniques such as pan coating can be used in which materials are deposited by successsive spraying of the polymer solution on the drug, or solute, accompanied by tumbling in a rotating pan. Other standard manufacturing procedures are described in *Modern Plastics Encyclopedia,* Vol. 46, pages 62 to 70, 1969; and in *Pharmaceutical Sciences,* by Remington, 14th Ed., pages 1626 to 1678, 1970, published by Mack Publishing Company, Easton, Pa. Generally, the exterior and interior wall will be about 2 to 6 miles thick. Of course, thinner and thicker walls are within the scope of the invention.

Exemplary solvents suitable for manufacturing the walls include inert inorganic and organic solvents that do not adversely harm the wall forming materials, the drug, the agent, and the final device. The solvents broadly include aqueous solvents, alcohols, ketones, esters, ethers, aliphatic hydrocarbons, halogenated solvents, cycloaliphatic aromatics, heterocyclic solvents, and mixtures thereof. Typical solvents include acetone, diacetone alcohol, methanol, ethanol, isopropyl alcohol methyl acetate, ethyl acetate, methyl isobutyl ketone, n-hexane, ethylene glycol monoethyl acetate, carbon tetrachloride, methylene chloride, ethylene dichloride, propylene dichloride, cyclohexane, mixtures such as acetone and water, acetone and methanol, acetone and ethyl alcohol, methylene dichloride and methanol, ethylene dichloride and methanol, and mixtures thereof.

DESCRIPTION OF EXAMPLES OF THE INVENTION

The following examples are merely illustrative of the present invention, and they should not be considered as limiting the scope of the invention in any way, as these examples and other equivalents thereof will become more apparent to those versed in the art in the light of the present disclosure, the drawings and the accompanying claims.

EXAMPLE 1

An osmotic delivery device for delivering potassium chloride at an osmotically-controlled rate is made as follows: first, 500 mg of commercially-available, dry powdered potassium chloride is compressed by standard compression techniques using a ⅜ inch punch. The compressed mass is then coated with a 3.5 mil thick of the inner wall forming polymer, consisting of commercially available cellulose acetate having an acetyl content of 38.3%. The wall is formed from a 80 to 20 parts by weight mixed methylene chloride-methanol solvent. A Wurster air suspension machine is used to form the wall. Next, the solvent is evaporated in an oven at 50° C. for 48 hours, and after cooling to room temperature, a 7.5 mil passageway is laser drilled through the wall. A drop of non-toxic blue dye is dropped onto the wall surface with the passageway as a guide for positioning the first compartment and the passageway in the first compartment.

Next, 250 mg of commercially available sucrose is compressed onto the surface with the passageway and the assembly returned to the air suspension machine. The assembly is then coated with exterior wall forming commercially available cellulose acetate having an acetyl content of 32%. A 5% polymer solution in dioxane is used to produce the exterior wall, which has a thickness of about 7 mils. After drying, a passageway is laser drilled through the exterior wall connecting the first, or osmotic solute compartment with the exterior of the device.

EXAMPLE 2

The procedure of Example 1 is repeated and the conditions are as disclosed, except that the drug compartment houses a glucocorticoid steroid selected from the group consisting of betamethasone, cortisone acetate, dexamethasone, fluprednisolone, hydrocortisone, methylprednisolone, paramethasone, prednisolone, prednisone and triaminicinolone hexacetonide, mixed with the osmotic effective solute fructose, and the first or solute compartment houses a mixture of the osmotically effective solutes sucrosefructose.

EXAMPLE 3

A non-stirring rate dependent osmotic device that releases a diluted drug solution independent of the pH of the environment is manufactured as follows: first, 125 mg of the diuretic ethacrynate sodium is compressed into a solid mass in a commercially available Manesty tableting machine to a Stoke's hardness of 8 kg. Next, the solid is coated in a standard air suspension machine with the semipermeable polymer cellulose acetate having an acetyl content of 38.3%. A 90% methylene chloride 10% methanol chloride solvent is used for forming the wall, and excess solvent is evaporated at 50° C. for 40 hours. The freshly formed wall has a thickness of 5 mils, and a 7 mil passageway is drilled through the wall.

Next, 350 mg of an osmotically effective composition consisting of dextrose and fructose is pressed in the Manesty machine to a Stoke's hardness of 8 kg. The pressed composition has a shape identical to the shape of the drug compartment. Then, a small drop of liquid cellulose acetate is spread around the outer edge of one surface of the pressed composition, and this surface is placed against the corresponding surface of the drug compartment with the passageway, with care taken to keep the passageway open. The two united masses are then coated in the air suspension machine with a wall of semipermeable acetate to a thickness of 10 mils. The wall is formed from a 5% solution consisting essentially of cellulose acetate having an acetyl content of 32%. The solution is made by dissolving 155 g of cellulose acetate in a solvent consisting of 3300 ml of acetone and 330 ml of water. The acetone and water have a 88.5 to 11.5 weight to weight basis. Finally, an osmotic passageway having a diameter of 10 mils is drilled through one exterior wall facing the mixed solutes for delivering diluted drug from the device.

EXAMPLE 4

The procedure of Example 3 is repeated in this example with conditions as described, except the drug in the drug compartment is a member selected from the group consisting of acetohexamide an ibuprofen mixed with the osmotic solute mannitol.

The novel osmotic system of this invention uses means for obtaining the delivery of drug at reduced concentrations to the environment of use while simultaneously maintaining the benefits of the drug and the integrity of the delivery device. While there are described and pointed out features of the invention as applied to presently preferred embodiments, those skilled in the art will appreciate that various modifications, changes, additions, and omissions in the devices illustrated and described can be made without departing from the spirit of the invention.

I claim:

1. An osmotic device for the controlled delivery of a beneficial drug to a biological environment of use, comprising:
   (a) an exterior wall formed of a semipermeable material permeable to the passage of an external fluid present in the environment and substantially impermeable to the passage of drugs and osmotically effective solutes, the exterior wall surrounding and forming;
   (b) a first compartment containing an osmotically effective solute that exhibits an osmotic pressure gradient across the wall against the exterior fluid;
   (c) a second compartment surrounded by an interior wall formed of a semipermeable material permeable to the passage of external fluid at a lower rate than through the exterior wall and substantially impermeable to the passage of drugs and osmotically effective solute, said compartment containing a drug;
   (d) a passageway in the exterior wall communicating the first compartment containing the osmotically effective solute with the exterior of the device;
   (e) a passageway in the interior wall communicating the second compartment containing drug with the first compartment containing the solute; and,
   (f) wherein, in operation when the device is in the fluid environment of use, fluid from the environment is imbibed through the wall into the first compartment and through the walls into the second compartment and (1) into the first compartment containing the solute in a tendency towards osmotic equilibrium at a rate determined by the permeability of the exterior wall and the osmotic pressure gradient across the wall thereby forming a solute solution, and into (2) the second compartment containing drug in a tendency towards osmotic equilibrium at a rate determined by the permeability of the interior and exterior walls and the osmotic pressure gradient across the wall thereby forming a drug solution, with drug solution osmotically delivered through the passageway from the second to the first compartment and diluted therein and osmotically delivered through the passageway from the first compartment to the exterior of the device.

2. The osmotic device for delivering the beneficial drug according to claim 1 wherein the device is sized, shaped and adapted as a dosage form for delivering drug to the gastrointestinal tract.

3. The osmotic device for delivering the beneficial drug according to claim 1 wherein the device is sized, shaped and adapted as a dosage form for delivering drug to the ano-rectal canal.

4. The osmotic device for delivering the beneficial drug according to claim 1 wherein the drug is a member selected from the group consisting of anticonvulsant, antiparkinson, analgesic, anti-inflammatory, anesthetic, hormonal, contraceptive, sympathomimetic, diuretic, ophthalmic, nervous system, sedative, tranquilizers, anti-infective and hypoglycemic.

5. The osmotic device for delivering the beneficial drug according to claim 1 wherein the drug in the second compartment is mixed with an osmotically effective solute.

6. The osmotic device for delivering the beneficial drug according to claim 1 wherein the exterior wall is formed of a member selected from the group consisting of cellulose acyltate, cellulose diacyltate, cellulose triacyltate, cellulose ether, cellulose esters and the interior wall is formed of a different member selected from the group consisting of cellulose acyltate, cellulose diacyltate, cellulose tracyltate, cellulose ether and cellulose esters.

* * * * *